(12) United States Patent
Barker et al.

(10) Patent No.: US 10,898,366 B2
(45) Date of Patent: Jan. 26, 2021

(54) WEARABLE GARMENT AND ITS USE IN PREVENTING STRETCH MARKS

(75) Inventors: Stephen George Edward Barker, Surrey (GB); Daryl M. Stutchbury, East Sussex (GB); Robert Albert Brown, Watford (GB)

(73) Assignees: STUFF OF LIFE LIMITED, Mayfield East Sussex (GB); UCL BUSINESS PLC, London (GB)

( * ) Notice: Subject to any disclaimer, the term of this patent is extended or adjusted under 35 U.S.C. 154(b) by 0 days.

(21) Appl. No.: 13/636,516

(22) PCT Filed: Mar. 10, 2011

(86) PCT No.: PCT/GB2011/050471
§ 371 (c)(1),
(2), (4) Date: Nov. 20, 2012

(87) PCT Pub. No.: WO2011/117603
PCT Pub. Date: Sep. 29, 2011

(65) Prior Publication Data
US 2013/0165018 A1    Jun. 27, 2013

(30) Foreign Application Priority Data
Mar. 24, 2010    (GB) .................................. 1004924.5

(51) Int. Cl.
*A41C 1/10*    (2006.01)
*A61F 5/03*    (2006.01)

(52) U.S. Cl.
CPC .................. *A61F 5/03* (2013.01); *A41C 1/10* (2013.01); *A41B 2400/32* (2013.01)

(58) Field of Classification Search
CPC .......... A61F 5/03; A41C 1/10; A41B 2400/32
USPC ..... 450/81, 97, 106, 112, 18, 19, 20, 34, 65, 450/66, 67, 68, 74, 75; 2/220, 221, 234, 2/239, 240, 260, 260.1, 337, 170, 152.1, 2/338
See application file for complete search history.

(56) References Cited

U.S. PATENT DOCUMENTS

| | | | | |
|---|---|---|---|---|
| 1,605,959 A * | 11/1926 | Lefevre | ......................... | 601/143 |
| 2,154,831 A * | 4/1939 | Booharin | ...................... | 601/143 |
| 2,787,792 A * | 4/1957 | Mikottis | ........................... | 2/221 |
| 2,830,591 A * | 4/1958 | Spanel et al. | .................. | 450/97 |
| 2,988,087 A * | 6/1961 | Krieger | .......................... | 450/81 |
| 3,080,869 A * | 3/1963 | Alberts | ........................ | 450/118 |
| 3,273,563 A | 9/1966 | Bonang | | |
| 3,662,760 A * | 5/1972 | Erteszek | ....................... | 450/111 |
| 4,506,390 A * | 3/1985 | Stern | ................................. | 2/221 |
| 4,697,592 A | 10/1987 | Maddux et al. | | |
| 5,016,291 A * | 5/1991 | Capper | ............................. | 2/312 |
| 5,897,423 A * | 4/1999 | Rosenberg | .................... | 450/115 |
| 5,948,707 A * | 9/1999 | Crawley et al. | ............. | 442/101 |
| 7,025,738 B2 * | 4/2006 | Hall | ................................. | 602/75 |

(Continued)

FOREIGN PATENT DOCUMENTS

JP            3147859        12/2008

*Primary Examiner* — Katharine Gracz
(74) *Attorney, Agent, or Firm* — Saliwanchik, Lloyd & Eisenschenk

(57) ABSTRACT

A band (1) comprising, on its inner surface, an irregular array of tacky areas or protrusions (6) that dissipate foci of stress in the skin (of the abdominal wall or other body areas). Wearing such a band around the abdomen is intended to help prevent the occurrence of stretch marks.

2 Claims, 3 Drawing Sheets

(56) References Cited

U.S. PATENT DOCUMENTS

| | | |
|---|---|---|
| 7,181,775 B2 | 2/2007 | Carney |
| 7,676,852 B1 | 3/2010 | Carney |
| 8,191,177 B1 | 6/2012 | Carney |
| 2011/0230119 A1 | 9/2011 | Thompson |

* cited by examiner

WEARABLE GARMENT AND ITS USE IN PREVENTING STRETCH MARKS

CROSS REFERENCE TO A RELATED APPLICATION

This application is a National Stage Application of International Application Number PCT/GB2011/050471, filed Mar. 10, 2011; which claims priority to Great Britain Application No. 1004924.5, filed Mar. 24, 2010; which are incorporated herein by reference in their entirety.

FIELD OF THE INVENTION

This invention relates to a device that has medical and cosmetic utility, and in particular to a device, in the form of a band or garment that can be worn, that can be used to help prevent or reduce the appearance of stretch marks.

BACKGROUND OF THE INVENTION

Stretch marks typically occur around the abdomen during periods of rapid growth in that area. In particular, they appear during the second and third trimesters of pregnancy, and in the development of obesity, particularly in older children and adolescents. They can also occur on the arms, the upper thighs and the breasts. Although they are not immediately threatening, and would not generally be classified as a therapeutic condition, they may have undesirable implications for the subject. They are certainly unsightly, and their prevention/mitigation is the subject of a valuable cosmetics industry. However, there is little or no evidence that the creams that are widely sold, to pregnant women in particular, have any effect. Indeed, a proper understanding of the likely cause of stretch marks, i.e. that the body has undergone an irreversible structural change, suggests that topical application of a cream is unlikely to have any effect.

Various devices are known, intended to be worn in contact with the abdomen, and that may have a local effect. For example, WO2008/131307 discloses a band having internal "pressure applicators" to be pressed against the body, for muscle support. See also US2009/0192423.

GB2152383A discloses a belt having a protuberance that is held against the abdomen, providing pressure that is intended to decrease the wearer's appetite and the ability of the wearer's stomach to hold large amounts of food. JP10234757A discloses a similar belt, for a similar purpose, having a plurality of protrusions in an array that may be regular or, even if irregular, includes spaces between the protrusions that allow straight lines to be drawn between them.

SUMMARY OF THE INVENTION

Although stretch marks are visible because of a thinning of the outer layers of skin, the present invention is based on the realisation that they may be caused by propagation, probably starting from a single point of stress weakness in fibrous connective tissue, e.g. collagen, below the skin. It is noteworthy that stretch marks almost invariably lie substantially vertically, although they may curve inwards slightly, especially towards the groin, reinforcing the propagation theory, and against the direction of known lines of skin formation and collagen deposition (Langer's lines).

The present invention is based at least in part on the hypothesis "that a focus of stress builds in the skin at a specific point (in a pregnant woman, for example, due to forces exerted from the growing child within), that becomes akin to a stress fracture. The skin "breaks" but, because of its living nature, only partly tears, giving rise to an irregular, red, warm, typically itching stretch mark that propagates vertically downwards (against the pattern of Langer's lines). The invention has as its aim the prevention or dissipation of foci of stress, e.g. in the abdominal wall, that might form the starting point for a stretch mark to develop.

A band according to the invention comprises, on its inner surface, an irregular array of tacky areas, e.g. in the form of protrusions, that aim to dissipate such foci of stress building in the skin. Such a band can be used for therapeutic and/or cosmetic purposes, to prevent or reduce the likelihood of stretch marks around the abdomen or elsewhere.

DESCRIPTION OF THE INVENTION

Figure 1:
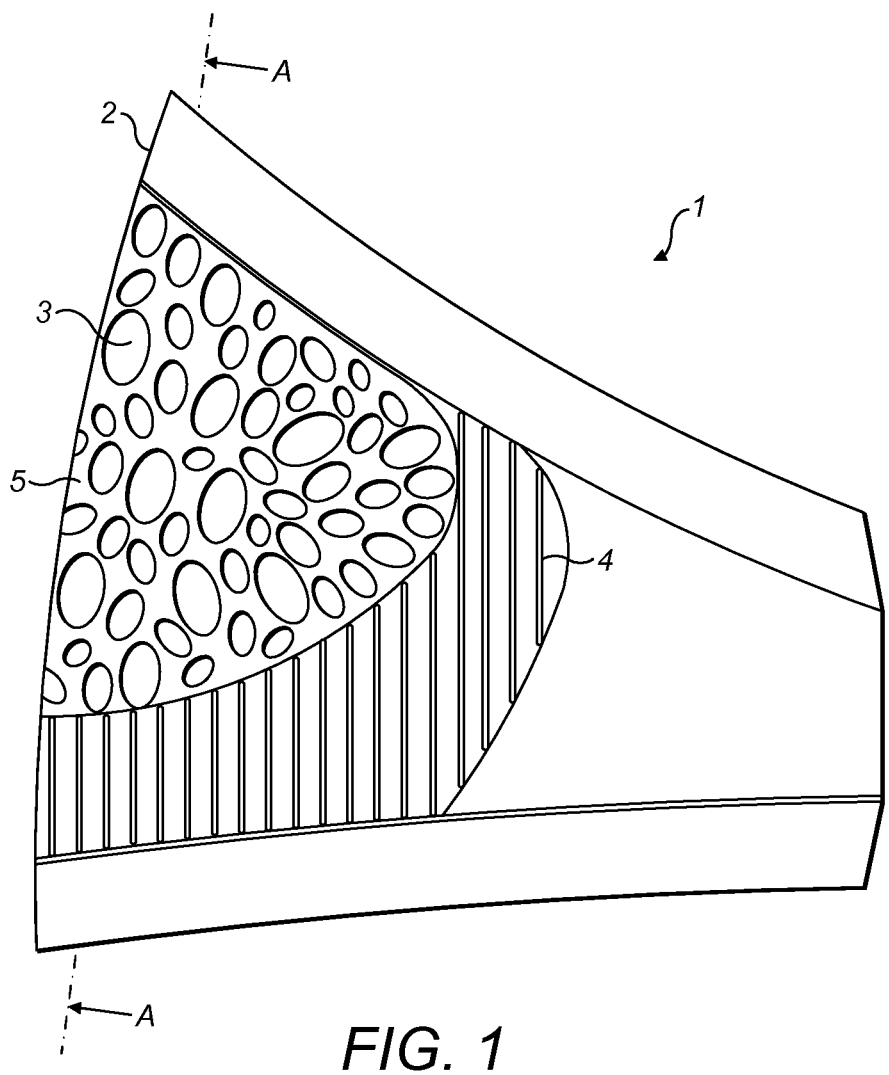
FIG. 1 is a schematic view of the outside of a band embodying the present invention.

A band of the invention may be designed to fit around a part of the body, e.g. arm, upper thigh or abdomen, that may be affected. It may be part of a larger garment. For example, the term "abdominal band" is used herein to describe any seamed or seamless band, belt or other garment that can be fitted around the abdomen. It may be elasticated for good contact with the skin, or may have fastening, e.g. a clasp or Velcro fastening, for fitting it around the abdomen.

The material of the band may be any that is typically used for such garments. The structure of the garment may be adapted to accommodate growth, e.g. during pregnancy. According to the invention, such a garment is modified by the provision of an irregular array of tacky areas or protrusions, e.g. random dots of a material, e.g. a plastics material such as silicone.

It will be evident to one of ordinary skill in the art how the array should be provided in order to achieve the aim of dissipating foci of stress. The array should be such as to ensure that no straight line, can be drawn in the spaces between the areas in the array, preferably neither vertically nor horizontally (in use), or in any other plane or line.

The areas provided on the band are such that they provide a small degree of adherence to the skin, on contact. They are thus friction-creating, so that skin moves in contact with those areas, when the device is moved transversely, in contact with skin. This allows contact of the novel device and the body to accommodate stretching or other movement without introducing foci of stress.

Typically, the friction-creating areas are provided by protrusions or pads mounted on a substrate that is typically elasticated. The pads may be built up by depositing a suitable plastics or other material, e.g. by ink-jet printing or transfer application. Suitable materials include, for example, silicone, polyurethane or latex rubber. If the material, e.g. of the protrusions, is not itself tacky, the protrusions may be coated with an additional tacky substance.

It will be evident that part only of each pad or protruberance will come into contact with skin, in use. It will be appreciated that it is the contact areas that should meet the requirement that no straight line can be drawn across the array, normal to the band, in the spaces between the said areas, whereby the said areas function to dissipate foci of stress in the skin As indicated above, a substrate on which the friction-creating areas are formed may be elasticated. The choice of material for the substrate and for the protrusions may be such that they are naturally adherent; alternatively, a suitable adhesive may be used. The material substrate may be cut out in part of the friction-creating areas, i.e. beneath pads or protrusions.

The device is preferably to be used when the skin has been washed clean such that no grease is left on the skin surface that would minimize friction, which is desirable. Furthermore, it might be best used in conjunction with a skin 'lotion' that leaves a 'tacky' residue on the skin to create more friction with the device.

A range of sizes of the novel product may be required, to accommodate 'bumps' growing during pregnancy.

The invention has been described in terms of its utility in the prevention of stretch marks. It may be also used in wound care, e.g. to maintain the juxtaposition of skin on each side of a wound. Further uses include minimising scar formation, and the alleviation of pain from a healing, but tensioned scar.

Figure 2:
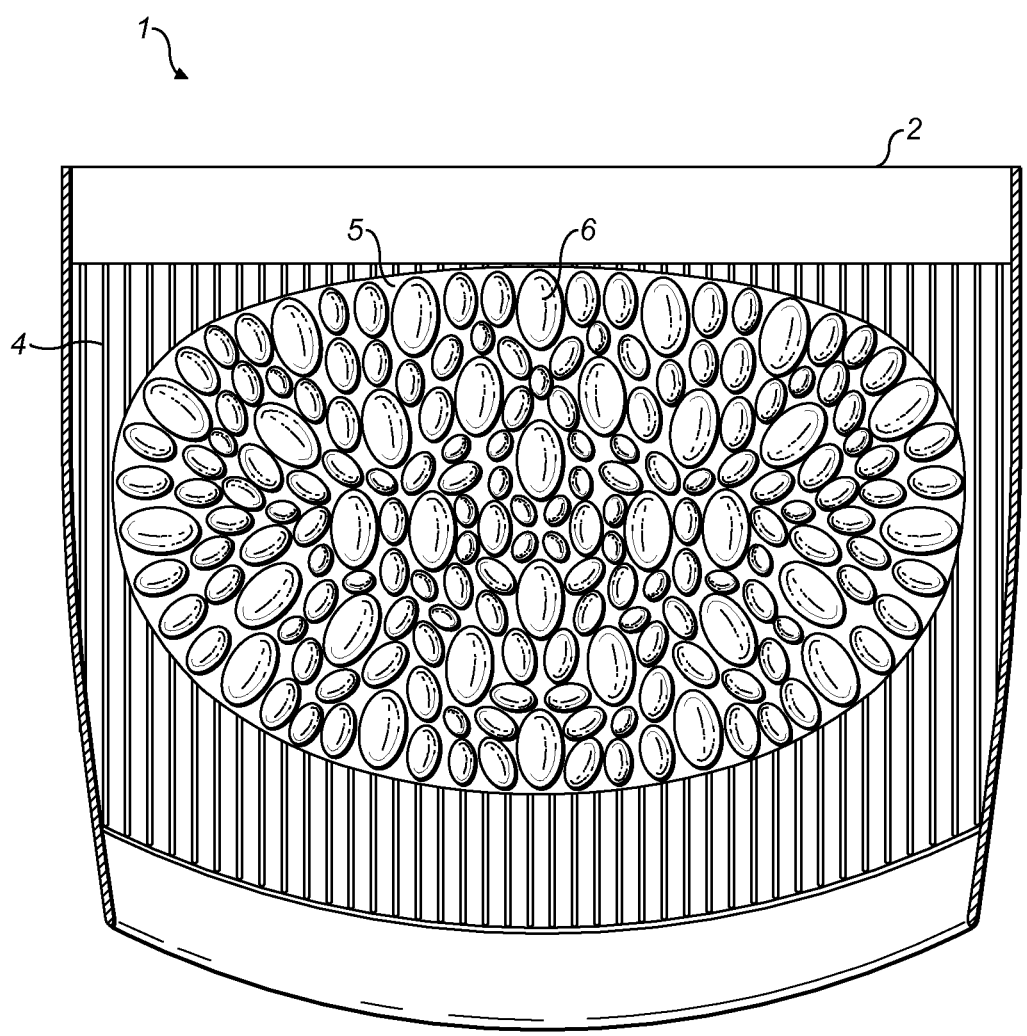
FIG. 2 is a view of the inside of a band as shown in FIG. 1 along the line A-A.
Figure 3:
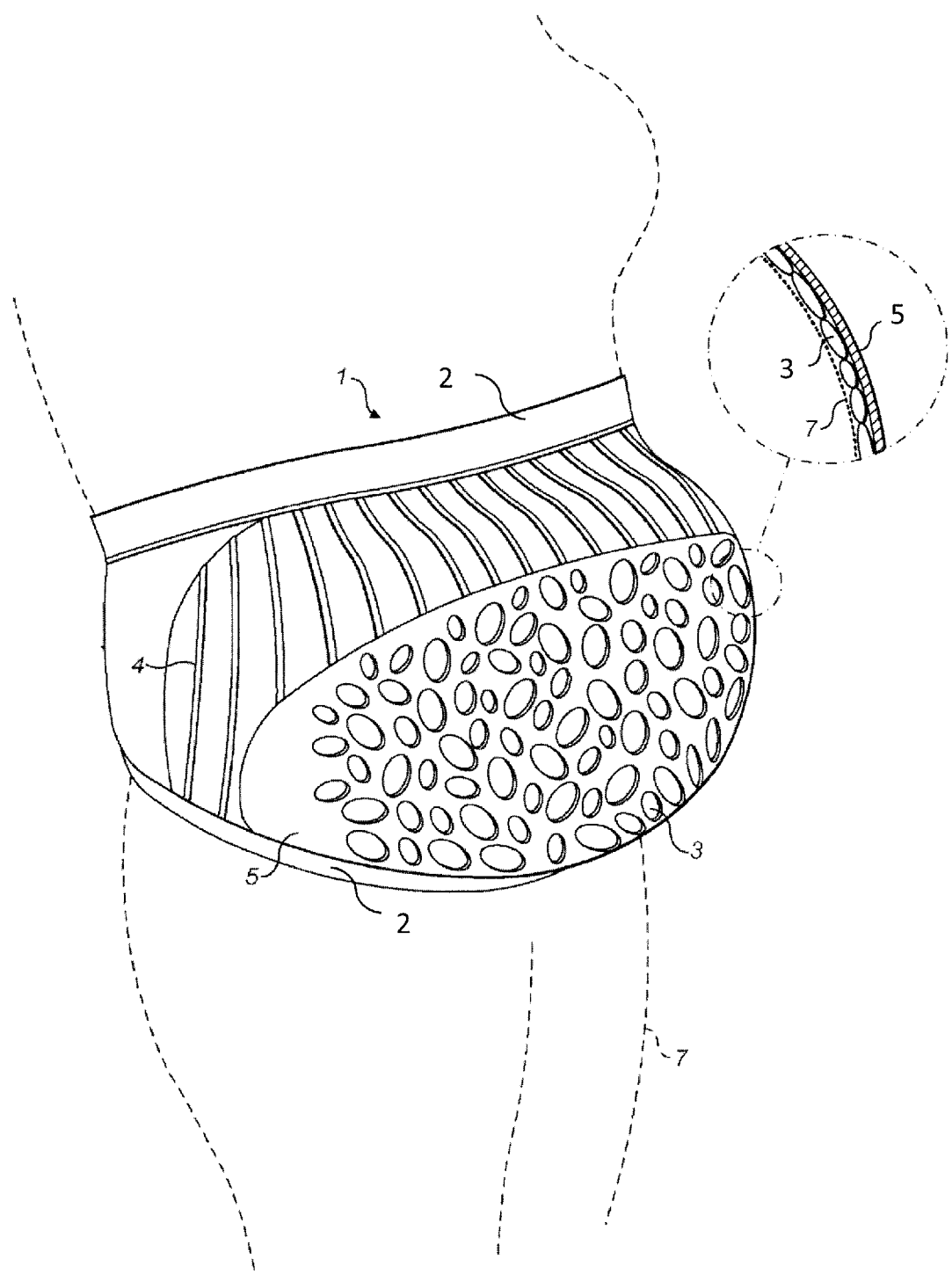
FIG. 3 is a view of the outside of the band, in use.

The invention will now be described by way of example only with reference to the accompanying drawings. FIG. 1 shows a band 1 comprising edge parts 2, apertures 3 in an elasticated section 4, the apertures 3 being in a part 5 of the elasticated section. As shown in FIG. 2, the apertures 3 are located underneath what is carried on one side of the band, i.e. a random array of tacky protuberances 6; that side is intended to be in contact with the skin 7 of a wearer, as shown in FIG. 3.

A device of the invention and as illustrated has been tested for 'wearability'. The results were positive. Over 50% of users said that the band was comfortable to wear all week. Over 50% of users felt that the band was comfortable, as it stretched during pregnancy. Over 80% of users would use the band again if they were pregnant. Over 90% of the sample thought that the band could help prevent stretch marks during pregnancy.

An experiment has been conducted, to test whether the garment altered the vector pattern of forces and distortions on an underlying structure aiming to mimic the pregnant abdomen. Specifically, it was determined whether the structure and adhesion of the garment to an underlying 'tissue' result in asymmetric (anisotropic) deformation.

A thin-walled football bladder was inflated inside the garment such that the two fitted tightly together. It was clear that there was good traction (high friction) between the pads of the garment and the ball, based on the squeaking noises as grip shifted during inflation.

The pattern of distortion of the ball alone during inflation was determined by marking the ball with tippex dots, inflating one pump-stroke at a time, and measuring (from photographs) the increase in spacing between dots in two planes, parallel and normal to the ball's nominal axis. This progressive stretching (percentage strain) in each plane (one point for each pump stroke) increased linearly with each stroke, with almost identical values. This identity means that expansion was almost perfectly symmetric (isometric), as expected for a spherical ball.

In the normal plane, a strain plot with respect to the number of strokes coincided with expansion of the ball only. However, in a plot of expansion parallel to the ball axis, the expansion deviated significantly from that expected This means that the garment had altered the symmetry of ball expansion, causing less deformation (over a wide strain range) in the parallel plane than in the normal plane. This is consistent with the proposition that the garment will substantially change and disrupt the pattern of strain direction in adjacent tissue (skin). In this case, it reduced the strain in the plane running from top to bottom of the garment (this is the vertical plane for the wearer).

The invention claimed is:

1. A method for preventing or reducing the likelihood of stretch marks on a subject, which comprises the subject wearing a band comprising,
a first edge, a second edge, and
an inner surface between the first edge and the second edge,
wherein said inner surface has an array of tacky pads arranged on the inner surface and between said first edge and said second edge, wherein the tacky pads are arranged separately to one another, with spaces therebetween, such that they do not touch and such that it is not possible to draw a continuous straight line starting from said first edge and crossing said second edge only within the spaces between the tacky pads wherein the straight line does not cross at least one of said tacky pads, and wherein each of said tacky pads forms a friction-creating contact adapted to adhere to skin so that skin in contact with the tacky pads moves with the tacky pads and the tacky pads function to dissipate foci of stress in the skin, thereby inhibiting the formation of stretch marks; wherein the band is worn by a subject in the second or third trimester of pregnancy on an area at risk of developing stretch marks.

2. The method, according to claim 1, wherein the tacky pads comprise at least one of a silicone, polyurethane, or latex rubber material.

* * * * *